(12) United States Patent
Nakanishi et al.

(10) Patent No.: US 6,562,744 B1
(45) Date of Patent: May 13, 2003

(54) PROCESS FOR PRODUCING INORGANIC POROUS MATERIAL IN A CAPILLARY

(75) Inventors: Kazuki Nakanishi, Kyoto (JP); Naohiro Soga, Kobe (JP); Tokiyo Minakuchi, Kyoto (JP)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/600,789

(22) PCT Filed: Dec. 17, 1998

(86) PCT No.: PCT/EP98/08295

§ 371 (c)(1),
(2), (4) Date: Jul. 21, 2000

(87) PCT Pub. No.: WO99/38006

PCT Pub. Date: Jul. 29, 1999

(30) Foreign Application Priority Data

Jan. 23, 1998 (JP) .......................................... 10-011377

(51) Int. Cl.[7] .............................................. C03C 11/00
(52) U.S. Cl. ......................... 501/39; 501/12; 65/17.2; 65/22; 210/198.2; 428/34.4; 428/36.9
(58) Field of Search ............................ 428/36.9, 34.1, 428/34.4; 210/198.2; 65/17.2, 22, 17.1, 910; 501/11, 12, 39, 53, 80, 81; 264/413–430

(56) References Cited

U.S. PATENT DOCUMENTS

| | | | |
|---|---|---|---|
| 4,727,209 A | * | 2/1988 | Chao .......................... 585/466 |
| 5,192,351 A | | 3/1993 | Mather et al. ................ 65/18.1 |
| 5,624,875 A | * | 4/1997 | Nakanishi et al. ............. 501/39 |
| 5,647,979 A | | 7/1997 | Liao et al. ................ 210/198.2 |
| 5,869,152 A | * | 2/1999 | Colon ......................... 428/34.4 |
| 5,875,564 A | * | 3/1999 | Kirkbir et al. ................. 34/305 |

FOREIGN PATENT DOCUMENTS

| WO | 95 03256 | 2/1995 |
|---|---|---|
| WO | 98 29350 | 7/1998 |

OTHER PUBLICATIONS

Jaymes I et al.: "New Aqueous Mullite Precursor Synthesis. Structural Study by Al and Si NMR Spectroscopy" Journal of the European Ceramic Society, vol. 16, No. 2, 1996 pp. 155–160.

* cited by examiner

Primary Examiner—Harold Pyon
Assistant Examiner—Walter B. Aughenbaugh
(74) Attorney, Agent, or Firm—Millen, White, Zelano & Branigan, P.C.

(57) ABSTRACT

Inorganic porous materials contained in a confined space with at least one dimension of less than 1 mm, which are in liquid tight contact with the walls of said confined space. Preferred as the confined space are capillaries. Articles contained such materials and methods for making them in the confined space are described.

16 Claims, 2 Drawing Sheets

PROCESS FOR PRODUCING INORGANIC POROUS MATERIAL IN A CAPILLARY

FIELD OF THE INVENTION

The present invention is related to a process for producing inorganic porous materials in a capillary (or more generally in a confined space as defined below) and materials prepared by such process. These materials are favorably applied to producing capillary columns for electrochromatography, porous catalysts, or enzyme supports. Such inorganic porous columns can be favorably applied to liquid, gel-permeation and gas chromatography. These columns can be used unmodified or modified e.g. by covering their surface with molecules like hydrophobic hydrocarbon ligands (e.g. octadecyl ligands) or like hydrophilic ligands like 2,3-dihydroxypropyl derivatives. The ligands of such modified columns can be further modified using known procedures. Porous catalysts or enzyme supports can be prepared by adding enzymes, e.g. glucose isomerase, or catalytic metal elements, e.g. platinum and palladium.

BACKGROUND OF THE INVENTION

The sol-gel method is one of liquid phase reaction paths to produce inorganic porous materials, especially silica gels. The sol-gel method denotes widespread processes in which polymerizable low molecular weight species are first generated, and through polymerization reactions, aggregated or polymerized materials are finally obtained. For example, the sol-gel method can be applied by hydrolyzing metal alkoxides, metal chlorides, metal salts or coordinated compounds which typically contain carboxyl or beta-diketone ligands. A process of this kind is disclosed in EP 0 363 697. In this process an organic polymer is used, which is compatible with the solution of the metal alkoxide or its polymer, and which undergoes phase separation during the hydrolysis-polymerization step. The materials produced by this process display connected open pores with a narrow range of the pore size distribution. Improvements to the process as disclosed in EP 0 363 697 are subject matter of WO 95/03 256 and WO 98/29 350. WO 95/03 256 disclose the use of special pore forming agents, whereas WO 98/29 350 disclose the use of precursors of such pore forming agents. All three documents disclose procedures useful to produce monolithic porous bodies. Common to the procedures disclosed in these three documents is that the porous formed body produced is taken out of the cast used for forming it. Such a procedure is not amenable if the porous formed body has a small dimension in at least one direction, because such thin structures would easily be teared or break. On the other hand the procedures disclosed in these three documents do not yield porous bodies which are fit liquid tight to their cast, because the inorganic material shrinks considerably during processing.

The existing capillary columns for electrochromatography is produced by packing inorganic materials such as silica gel beads into a capillary by physical means. It is necessary for the column packing materials used in the electrochromatography to carry electrostatic charge on their surfaces. Accordingly, inorganic porous materials which retain stable negative charges in a neutral pH condition, especially silica gels, are widely used.

Particle-packed capillary columns for electrochromatography have been prepared by physically packing inorganic particulate materials into a capillary. In order to avoid the change in the packing state of the particles due to their motion in the capillary, the both ends of a capillary are fitted with the parts called "frit" with relatively low porosity.

Particle-packed capillary columns are disadvantageous in the points that: (a) the packing procedure is complicated and time-consuming. (b) the reproducibility of the packing state, and correspondingly that of an excellent analytical performance, is poor. (c) Since the homogeneous packing of an entire capillary becomes increasingly difficult as the column length increases, an improvement of the analytical performance by increasing the total column length is not practical.

In addition, particle-packed capillary columns equipped with the frits at both ends frequently causes bubbling at the space between the frit and packed-beds, thus requires additional pressurization to the normal chromatographic operation.

In spite of the fact that the analytical performance of a capillary column is governed by its inner porous structure directly related to the packing state of the particles, there has been no established particle-packing method which produces the stable and reproducible packing state.

SUMMARY OF THE INVENTION

Figure 1:
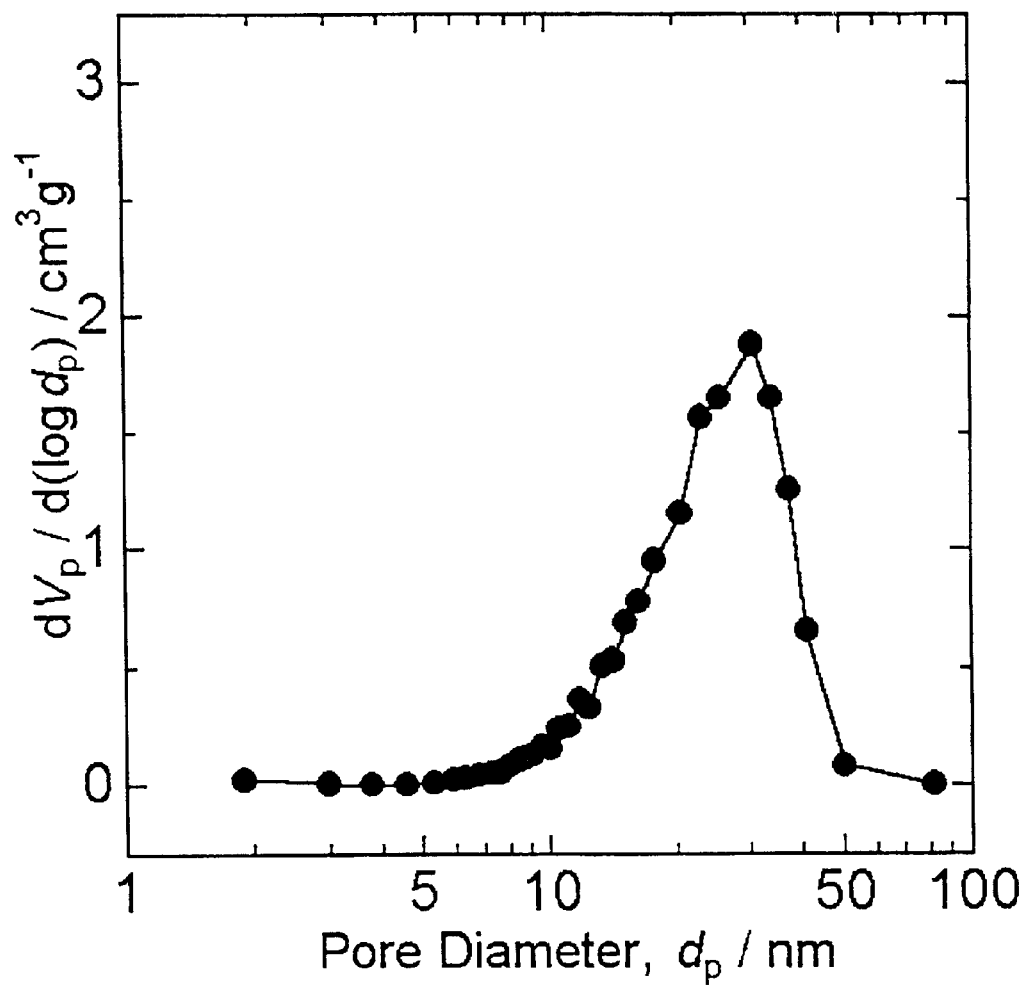
FIG. 1 shows the size distribution of mesopores measured for a sample gel prepared according to Example 1.

The problem of the present invention is to provide monolithic porous bodies with at least one small dimension, which are useful e.g. as sorbents in micro scale separations or as support media for catalysts or immobilized enzymes.

THIS PROBLEM IS SOLVED BY THE PRESENT INVENTION

The present inventors have found that: A capillary column which exhibits homogeneous and continuous double pore structure through the whole length of the capillary can be obtained by the processes of; 1) to form a three-dimensional co-continuous network consisting of an inorganic gel phase and a solvent phase both having average domain size of larger than 100 nm via a sol-gel process from a solution precursor containing a thermally decomposable component in a capillary with the inner diameter of less than 1 mm, 2) to modify the nanometer-range microstructures by heating the wet gel to decompose said thermally decomposable component, 3) to dry and heat-treat the gel to obtain completely inorganic porous material.

A capillary with an inner diameter of less than 1 mm as mentioned above is the prefered modification of the invention, e.g. the specialized case of a confined space with a small dimension in at least one direction as defined in the problem to be solved by the invention. Accordingly unless explicitly stated, a capillary can be replaced by any other confined space with a small dimension in at least one direction. In this context a small dimension is defined as less than 1 mm, preferably between 10 and 200 $\mu$m. Other examples of confined spaces with a small dimension in at least one direction are: three- or four-sided prisms or thin plates. Typically at least one dimension, e.g. the length of these structures, can be larger, separation capillaries might be one or several centimeters long, or even longer. Plates would be thin (less than 1 mm), but could be broader than 1 mm, e.g. one or several centimeters, up to about 20 cm broad. In all cases the porous formed body is enclosed by such a confined space, whereby a liquid tight contact area between porous formed body and confined space is provided.

The present invention has been developed based on the above knowledge. The invention provides capillary columns with a well-defined and highly reproducible internal pore structure through the whole length of the capillary and with an excellent analytical performance; instead of those packed with particles by conventional physical methods which has been defective in homogeneity, reproducibility and analytical performance.

DETAILED DESCRIPTION OF THE INVENTION

One means of the present invention to attain said object is characterized by previously dissolving a thermally decomposable compound in a reaction solution, forming, from said reaction solution through its sol-gel conversion in a capillary, a gel that comprises a solvent-rich phase containing three-dimensionally networked open pores having a mean pore diameter of not smaller than 100 nanometers and an inorganic substance-rich skeleton phase containing particles each having fine pores on its surface, then heating the wet gel to thermolyze said thermally decomposable compound existing in the reaction system, and thereafter drying and heating the gel.

In one preferred embodiment of said means, silica $SiO_2$ is used as the inorganic substance while an amide compound, such as urea, capable of making the reaction system basic through its thermolysis is used as the thermally decomposable, low-molecular compound.

Another means of the present invention also to attain said object is characterized by dissolving a water-soluble polymer and a thermally decomposable compound in an aqueous acidic solution, adding thereto a metal compound having hydrolyzable functional groups to thereby hydrolyze said compound, solidifying the resulting product in a capillary, then heating the wet gel to thereby thermolyze the thermally decomposable low molecular compound existing in said gel, and thereafter drying and further heating the gel.

The substance to be added to the starting metal alkoxide is one having the function of inducing both sol-gel conversion and phase separation at the same time. Using this, the reaction system is separated into a solvent-rich phase and a skeleton phase, which are gelled. As the substance of that type, preferred is a polymer soluble in solvents, such as polyethylene oxide, polyvinyl pyrrolidone, polyethylene imine and polyallylamine.

The metal alkoxide is preferably a silicon alkoxide, which may include, for example, tetramethoxysilane, tetraethoxysilane, methyltrimethoxysilane, ethyltrimethoxysilane and vinyl trimethoxysilane. However, these are not limitative. The metallic elements corresponds to those contained in the desired oxide phase can be Si, Ti, Zr or Al. Both alkoxides containing single or multiple kinds of metals can be used. The oligomers of the alkoxides, usually up to decamers, can be used as far as they dissolve or disperse homogeneously in the solvent alcohol.

The acidity of the aqueous solution used to hydrolyze the metal alkoxide is preferably stronger than 0.001 mol/L of mineral acid such as hydrochloric acid or nitric acid.

The capillary, made of fused silica for example, should have an inner diameter of less than 1 mm, preferably between 10 and 200 μm. Similarly, instead of capillaries, containers which form inside them thin prisms of similar dimensions or thin plates with a thickness of less than 1 mm can be used.

The capillary, made of fused silica for example, should have an inner diameter of less than 1 mm, preferably between 10 and 200 μm. Similarly, instead of capillaries containers which form inside them thin prisms of similar dimensions or thin plates with a thickness of less than 1 mm can be used.

For the liquid tight junction between rod and capillary, the capillary wall should have high affinity with the gelling silicate components components in the solidifying solution. For example; (1) materials with surface hydroxyl groups which can undergo condensation with silanols, (2) relatively polar organic polymer surfaces which can physically adsorb silicate oligomers, (3) any other material which is surface-treated with hydrophilic layers; all of these can realize the liquid tight junction. Materials with very high water-repellency, such as PTFE resin or surfaces modified with fluorine-containing reagents, are not appropriate to make the liquid tight junction by the chemical means described above. In this special case, the use of thermoshrinking PTFE resin makes it possible to physically liquid tight clad after the formation of the gel body inside the capillary, by heating the resin capillary up to around 300° C. so as to obtain satisfactory cladding. The dimension of the confined space, diameter of a capillary or gap between the parallel walls etc., should be in the size range smaller than 1 mm and preferably smaller than 100 microns.

The hydrolysis and polycondensation reaction is conducted under the conditions of; temperature between 40 and 80° C., reaction time between 0.5 and 5 hours. The hydrolysis and polycondensation follows the steps of; 1) initially transparent solution becomes gradually opaque due to the phase separation into a gel phase and a pore-forming phase, 2) the whole solution turns into gel. During the whole reaction steps the water-soluble polymer is molecularly dissolved in the solution and no effective precipitation occurs.

One embodiment of the present invention for producing a porous inorganic material, in which the pore structure of the porous inorganic material can be most effectively controlled, is sol-gel conversion which comprises starting from a metal alkoxide and adding a suitable substance to said starting compound to thereby give a structure of a solvent-rich phase that produces macro-pores.

In the method of the present invention, where a water-soluble polymer and a thermally decomposable compound are dissolved in an aqueous acidic solution and a metal compound having a hydrolyzable functional group is added thereto to thereby hydrolyze said metal compound, formed is a gel comprising a solvent-rich phase and a skeleton phase as separated from each other in the capillary. After the product (gel) is solidified and then ripened for a suitable period of time, the wet gel is heated whereby the thermally decomposable compound that has been previously dissolved in the reaction system is thermally decomposed, resulting in the increase in the pH of the solvent that is kept in direct contact with the inner walls of particles constituting the skeleton phase. As a result, the solvent corrodes said inner wall to thereby change the inner surface of said inner wall into a roughened one, whereby the pore-size of said particles is gradually enlarged.

For the gel consisting essentially of silica, the degree of said change in an acidic or neutral region will be very small, but with the increase in the thermolysis to enlarge the basic degree of the aqueous solution, the part constituting each pore is dissolved and re-precipitated to give a more flat part, thereby inducing more active reaction to enlarge the mean pore size.

If the gel has only fine and three-dimensionally restrained pores without having any macro-pores, even its part capable of being dissolved under equilibrated conditions could not produce a dissolved substance capable of being diffused into the external solution, so that the original fine pore structure will remain in the gel to have a relatively large proportion. As opposed to this, if the gel has a solvent rich-phase capable of giving macro-pores, it contains a large amount of only two-dimensionally restrained fine pores, so that the exchange of substances between said solvent-rich phase and the external aqueous solution may be effected well frequently in the gel, resulting in the removal of fine pores with the growth of macro-pores in the gel while preventing the entire pore size distribution of the resulting gel from being broadened.

In the thermolyzing step, it is effective to put the gel in a closed condition in order to make the vapor pressure of the thermally decomposed product saturated and to rapidly make the solvent have a steady pH-value.

Specific examples of the thermally decomposable compound employable herein may include urea, and organic amides such as formamide, N-methylformamide, N,N,-dimethylformamide, acetamide, N-methylacetamide, and N,N-dimethylacetamide. However, as will be mentioned in the Examples to follow hereinunder, the thermally decomposable compound is not limited to these, but may be any one capable of making the solvent basic after its thermolysis, since the pH value of the solvent after the thermolysis (final pH) is an important factor in the method of forming the mesopores. Similary, thermally-decomposable compounds which generate alternative substances which are capable of dissolving silica, e.g. hydrofluoric acid, can also be used. In addition, those capable of producing a compound having the property of dissolving silica, such as hydrofluoric acid, through thermolysis are also usable in the present invention. Such pore forming agents or precursors of pore forming agents are disclosed in WO 95/03 256 and in WO 98/29 350.

The amount of the thermally decomposable compound (precursor of pore forming agent) to be in the reaction system of the present invention may vary, depending on the type of said compound. For urea, for example, its amount may be from 0.1 to 2.0 g, preferably from 0.2 to 1.0 g, per 10 g of the reaction system. The heating temperature for the thermolysis of urea may fall between 60° C. and 200° C., and, after the thermolysis, the final pH of the solvent is preferably from 9.0 to 11.0.

After the dissolving and re-precipitating reaction has reached its steady condition, the thermolyzing time for obtaining the corresponding pore structure may vary, depending on the size of the intended macro-pores and the volume of the reaction system being processed. Therefore, it is important to determine the shortest thermolyzing time, over which the pore structure of the gel is no more substantially changed under the processing conditions. For example, where urea is used as the thermally decomposable compound and the thermolyzing temperature falls between 60 C. and 200° C., the thermolyzing temperature falls between 30 days (at 60° C.) to 100 hours (at 200° C.).

From the processed gel, the solvent is evaporated off, whereby the gel is dried to be a dry gel which is coherently attached to the inner wall of the capillary with the inner diameter of less than 1 mm. Since there is a probability that some starting compounds will still remain in the dry gel, the dry gel is thereafter heated at suitable temperatures to thereby further pyrolyze the remaining organic substances. As a result of the heat treatment, the intended porous inorganic material is finally obtained. Generally, the drying is conducted at the temperature between 40 and 100° C. for several to several tens hours, whereas the heat-treatment is performed in the temperature range between 300 and 700° C.

The porous inorganic materials to be obtained according to the method of the present invention have three-dimensionally networked, open through-holes of not smaller than 100 nm in diameter, and fine pores of from 5 to 100 nm in diameter as formed on the inner walls of said through-holes. The porous inorganic materials of the present invention can be used in manufacture of chromatography columns, adsorbent and filters, which, however, are not limitative.

Without further elaboration, it is believed that one skilled in the art can, using the preceding description, utilize the present invention to its fullest extent. The preferred specific embodiments and examples are, therefore, to be construed as merely illustrative, and not limitative of the disclosure in any way whatsoever.

The entire disclosures of all applications, patents, and publications cited above and below, and of corresponding Japanese Application number JP-hei 10-11377, filed Jan. 23, 1998, are hereby incorporated by reference.

EXAMPLES

Example 1

Firstly, 0.90 g of poly(ethylene oxide) (product No. 85645-2, manufactured by Aldrich, Molecular weight: 10000) and 0.90 g of urea were dissolved in a 10 g of 0.01 mol/l aqueous solution of acetic acid. Then 4 ml of tetramethoxysilane was mixed with this solution under stirring to promote hydrolysis reaction. After a few minutes stirring, the resultant transparent reaction solution was transferred to a capillary with the inner diameter of 0.1 mm (100 $\mu$m) and sealed, which gelled in 30 min at a constant temperature oven kept at 40° C.

The solidified sample was further aged at the same temperature for several hours, then heated up to 120° C. and kept at the temperature for 1 h under tightly sealed condition. The pH of the solution in contact with the gel sample was 10.7. The gel was subsequently dried for 3 days and was heated up to 400° C. with the heating rate of 100° C./h. With these processes, a porous amorphous silica filled in a capillary with the inner diameter of 0.1 mm was obtained.

It was confirmed by the electron microscopic observation that in the porous silica material thus formed in the capillary, uniform macropores with a pore size of about 2.0 micrometer were present in an interconnected manner. In addition, the nitrogen adsorption measurement evidenced the existence of mesopores with average diameter of 25 nm in the inner wall of the said gel sample. FIG. 1 shows the pore size distribution of the mesopores.

In addition, when the porous materials were manufactured under the same conditions as described above except that the temperature of aging in tightly sealed condition was changed to 80° C. or 200° C., the distributions of the macropores were not affected, but the median size of mesopores measured by the nitrogen adsorption varied to about 15 nm and 50 nm for 80° C. and 200° C., respectively. From these results, it was shown that larger median size of mesopores can be obtained as the temperature of aging in tightly sealed condition increased.

The capillary column thus prepared, with the effective length of 25 cm, was set in an electrochromatography apparatus, and thiourea was analyzed at the temperature of 20° C. and with the applied electric voltage of 20 kV, adopting the mobile phase consisting of (acetonitrile: 50 mM of tris buffer solution)=80:20 adjusted at pH=8.

The linear velocity of electro-osmotic current obtained under the conditions specified above was 1.19 mm/s, which was comparable to those observed in well-packed conventional particle-packed capillary columns.

Figure 2:
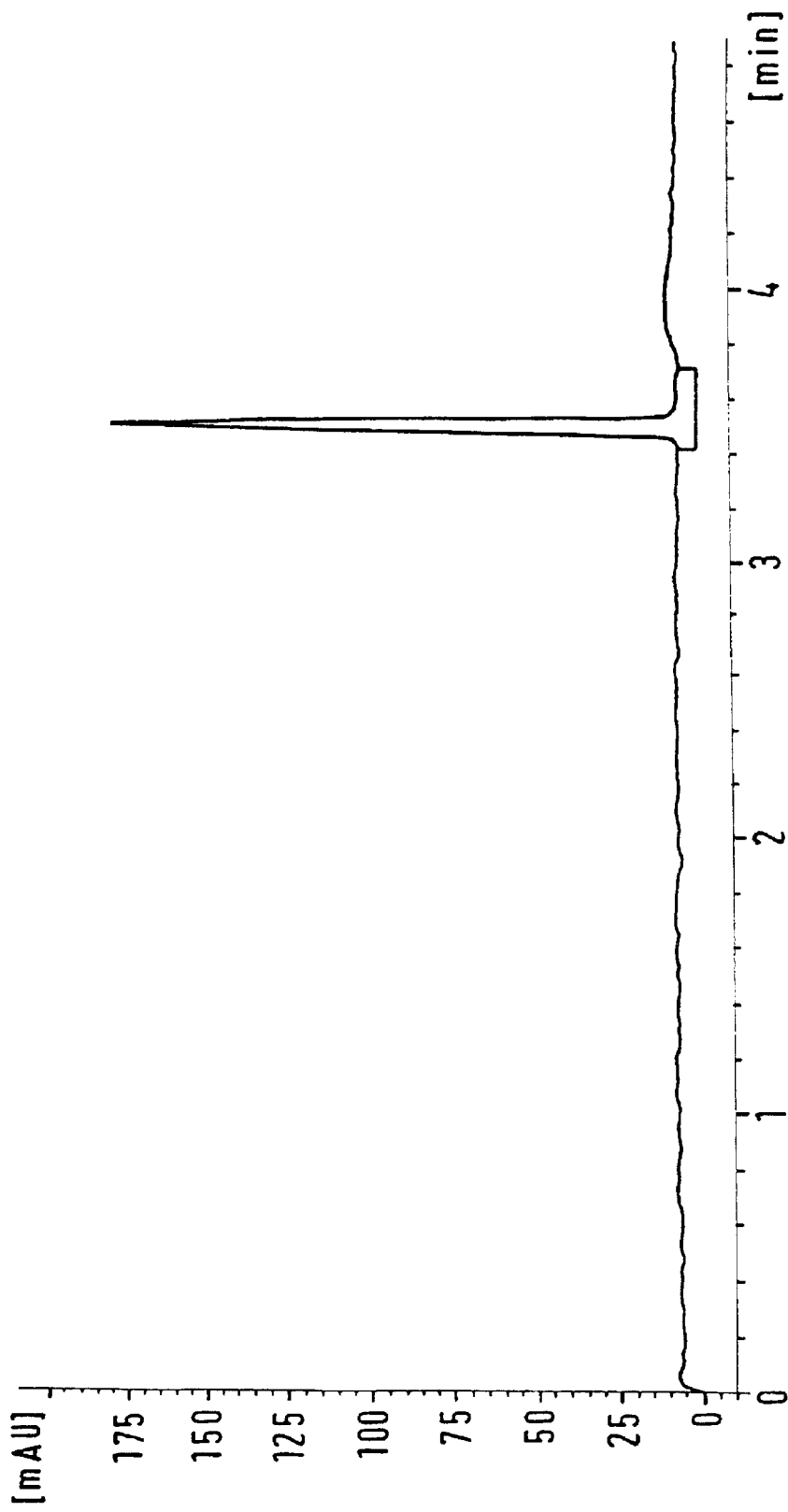
FIG. 2 shows the electrochromatogram of thiourea obtained using the capillary column described in Example 1.

FIG. 2 shows the elution peak of thiourea obtained under the conditions specified above. The number of theoretical plates calculated from the peak width was 48000 plates against 25 cm, which is comparable to the value of well-packed conventional particle-packed column; 200,000 plates/m.

Example 2

The capillary columns were manufactured under identical conditions to those described in Example 1 except that the amount of urea was 0.45 g to adjust the final value of the solution pH in contact with the gel sample to 9.

The median mesopore sizes of the resultant gels were 15, 25 and 50 nm at 80, 120 and 200° C., respectively. These results were in accordance with those obtained in the Example 1 within the range of experimental error, which implies that the median mesopore size hardly depend on the concentration of urea, but the widths of the mesopore size distribution became broader at all temperatures. These results show that with an increase in the concentration of urea in the starting solution, the mesopore distribution width became narrower and the specific mesopore volume became larger.

With the capillary columns thus obtained, it was possible to perform similar electrochromatographic separation of thiourea as described in the Example 1.

EFFECT OF THE PRESENT INVENTION

As described so far, according to the present invention, it is possible to manufacture porous materials with controlled pore distribution in a capillary with the inner diameter of less than 1 mm. Presently invented inorganic porous column has outstanding features owing to its double-pore structure comprising interconnected macropores and tailored mesopores; the column requires no physical packing procedure for its production and can be suitably applied as a monolithic capillary column for electrochromatography, capillary electrophoresis, solid phase micro-extraction and gas chromatograpy.

What is claimed is:

1. A process for producing an article comprising an inorganic porous material contained in a container having a confined space of at least one dimension less than 1 mm, which comprises:

providing an aqueous acidic solution comprising a water-soluble organic polymer, a thermally decomposable component and a metal compound having thermally hydrolyzable ligands, such that a sol-gel process of hydrolysis and polycondensation is initiated, either before or during the hydrolysis and polycondensation, filling at least part of the confined space of the container with the solution and allowing the hydrolysis and polycondensation to continue such that a three-dimensional co-continuous network of an inorganic gel phase and a solvent phase, both having a diameter of larger than 100 nm is formed from the solution, heating the container with the three-dimensional co-continuous network to decompose the thermally decomposable component, thereby modifying the nanometer-range microstructures, drying and heat-treating the resulting container with the three-dimensional co-continuous network to obtain a completely inorganic, solid porous material in liquid tight contact with the inner wall(s) of the confined space of the container.

2. The process of claim 1, wherein the metal compound having thermally hydrolyzable ligands is a silicon alkoxide or a soluble or dispersible oligomer thereof which is and the resulting inorganic, solid porous material is of silica.

3. The process of claim 2, wherein the thermally decomposable compound is urea.

4. The process of claim 2, wherein the thermally decomposable compound is a compound containing amide or alkylamide ligands.

5. The process of claim 1, wherein the a container having a confined space of at least one dimension less than 1 mm is a capillary having an inner diameter of less than 1 mm.

6. The process of claim 2, wherein the a container having a confined space of at least one dimension less than 1 mm is a capillary having an inner diameter of less than 1 mm.

7. The process of claim 1, wherein the formed inorganic, solid porous material is a three-dimensional network with open macropores of no smaller than 100 nm diameter and mesopores of 5–100 nm formed on the inner walls of the macropores.

8. The process of claim 1, wherein the water-soluble organic polymer is a polyethylene oxide, polyvinyl pyrrolidone, polyethylene imine or polyallylamine.

9. The process of claim 2, wherein the a container having a confined space of at least one dimension less than 1 mm is a capillary having an inner diameter of between 10 and 200 $\mu$m.

10. The process of claim 5, wherein the capillary is of a fused silica material.

11. The process of claim 10, wherein the inners wall of the capillary is treated to provide: a) surface hydroxyl groups which can condense with silanols, b) a polar organic polymer surface which can physically adsorb silicate oligomers, or c) a hydrophilic surface layer.

12. The process of claim 1, wherein the hydrolysis and polycondensation is conducted at a temperature of 40 to 80° C.

13. The process of claim 3, wherein 0.1 to 2.0 g of urea is used per 10 g of aqueous acidic solution.

14. The process of claim 1, wherein the heating of the container with the three-dimensional co-continuous network to decompose the thermally decomposable component is at a temperature of 60 to 200° C.

15. The process of claim 1, wherein the decomposition of the thermally decomposable component results in raising the pH of the solvent phase.

16. The process of claim 1, wherein the drying is conducted at a temperature of 40 to 100° C. and the subsequent heat-treating is conducted at 300 to 700° C. to pyrolyze any remaining organic substances.

* * * * *

UNITED STATES PATENT AND TRADEMARK OFFICE
CERTIFICATE OF CORRECTION

PATENT NO. : 6,562,744 B1 Page 1 of 1
DATED : May 13, 2003
INVENTOR(S) : Kazuki Nakanishi et al.

It is certified that error appears in the above-identified patent and that said Letters Patent is hereby corrected as shown below:

<u>Column 7,</u>
Line 57, delete "thermally";

<u>Column 8,</u>
Line 14, delete "thermally".

Signed and Sealed this

Eighteenth Day of November, 2003

JAMES E. ROGAN
*Director of the United States Patent and Trademark Office*